United States Patent
Yan et al.

(10) Patent No.: US 10,217,248 B2
(45) Date of Patent: Feb. 26, 2019

(54) METHOD FOR REMOVING STREAK FROM DETECTOR CELL WITH PERFORMANCE DIFFERENCE

(71) Applicant: General Electric Company, Schenectady, NY (US)

(72) Inventors: Ming Yan, Shanghai (CN); Kun Tao, Shanghai (CN); Hao Xu, Shanghai (CN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 277 days.

(21) Appl. No.: 15/507,077

(22) PCT Filed: Jul. 31, 2015

(86) PCT No.: PCT/US2015/043042
§ 371 (c)(1),
(2) Date: Feb. 27, 2017

(87) PCT Pub. No.: WO2016/032683
PCT Pub. Date: Mar. 3, 2016

(65) Prior Publication Data
US 2017/0256076 A1    Sep. 7, 2017

(30) Foreign Application Priority Data
Aug. 27, 2014 (CN) ............ 2014 1 0428793

(51) Int. Cl.
*A61B 6/00* (2006.01)
*G06T 7/00* (2017.01)
(Continued)

(52) U.S. Cl.
CPC ............ *G06T 11/005* (2013.01); *A61B 6/032* (2013.01); *A61B 6/5205* (2013.01); *G06T 7/0012* (2013.01); *G06T 2207/10081* (2013.01)

(58) Field of Classification Search
CPC ..... A61B 6/032; A61B 6/5205; G06T 11/005; G06T 2207/10081
See application file for complete search history.

(56) References Cited

U.S. PATENT DOCUMENTS 4,809,172 A * 2/1989 Hopkinson ........... G06T 11/005
378/4
5,416,815 A * 5/1995 Hsieh ................... G01N 23/046
378/4
(Continued)

FOREIGN PATENT DOCUMENTS

CN    102105106 A    6/2011
CN    102768759 A    11/2012
(Continued)

OTHER PUBLICATIONS

International Search Report and Written Opinion for corresponding PCT application No. PCT/US2015/043042 dated Nov. 4, 2015; 13 pages.

(Continued)

*Primary Examiner* — Gandhi Thirugnanam
(74) *Attorney, Agent, or Firm* — GE Global Patent Operation; William K. Baxter

(57) ABSTRACT

Embodiments of the present invention disclose a method for removing streaks from detector cells with performance difference, specifically a method for removing streaks from detector cells with performance difference and streaks caused by other reasons. The method comprises: estimating a projection on a detector cell with performance difference for each of one or more views; reconstructing one or more initial images with the estimated projection on the detector cell with performance difference for each view; estimating a projection error on the detector cell with performance difference for each view from the reconstructed one or more initial images having streaks; and reconstructing one or (Continued)

more output images with the estimated projection error on the detector cell with performance difference for each view to remove the streaks from the reconstructed one or more output images, improving quality of CT reconstructed images.

20 Claims, 7 Drawing Sheets

(51) Int. Cl.
*G06T 11/00* (2006.01)
*A61B 6/03* (2006.01)

(56) References Cited

U.S. PATENT DOCUMENTS

| | | | | |
|---|---|---|---|---|
| 5,680,426 | A * | 10/1997 | Ching-Ming | G06T 11/005 378/8 |
| 5,848,114 | A | 12/1998 | Kawai et al. | |
| 8,050,481 | B2 | 11/2011 | Reeves et al. | |
| 8,400,683 | B2 * | 3/2013 | Paul | H04N 1/506 358/1.9 |
| 8,737,711 | B2 | 5/2014 | Goto et al. | |
| 9,454,804 | B2 * | 9/2016 | Takahashi | A61B 6/032 |
| 2004/0081273 | A1 * | 4/2004 | Ning | A61B 6/032 378/37 |
| 2004/0234022 | A1 * | 11/2004 | Nukui | G06T 11/005 378/4 |
| 2013/0243349 | A1 * | 9/2013 | Yang | G06T 5/002 382/275 |
| 2014/0010431 | A1 * | 1/2014 | Stayman | G06T 7/0012 382/131 |
| 2014/0099011 | A1 * | 4/2014 | Begin | G06T 5/002 382/131 |
| 2014/0169520 | A1 * | 6/2014 | Langan | G01N 23/046 378/5 |
| 2015/0190106 | A1 * | 7/2015 | Yamakawa | A61B 6/032 378/4 |
| 2017/0256076 | A1 * | 9/2017 | Yan | A61B 6/032 |

FOREIGN PATENT DOCUMENTS

| | | |
|---|---|---|
| CN | 103083031 A | 5/2013 |
| CN | 103186883 A | 7/2013 |
| CN | 103366389 A | 10/2013 |
| JP | 2008104122 A | 5/2008 |
| WO | 2013146283 A1 | 10/2013 |

OTHER PUBLICATIONS

Hsieh, "Adaptive streak artifact reduction in computed tomography resulting from excessive x-ray photon noise", Medical Physics, Nov. 1998.

Jian-Wei et al., "The Review of Reasons and Correction Methods for Artifacts in ICT Images", CT Theory and Application, vol. No. 14, Issue No. 3, pp. 24-28, Aug. 2005.

Cheng et al., "Fast Iterative Adaptive Reconstruction in Low-Dose CT Imaging", Image Processing, IEEE International Conference on, Atlanta, GA, USA, pp. 889-892, Oct. 8-11, 2006.

Lemmens et al., "Suppression of metal streak artifacts in CT using a MAP reconstruction procedure", Nuclear Science Symposium Conference Record, San Diego, CA, USA, pp. 3431-3437, 2006.

Ying et al., "The research of streak artifact correcting method in CT reconstruction", Optical Technique, vol. No. 33, Issue No. 1, Jan. 2007.

Mouton et al., "An Experimental Survey of Metal Artefact Reduction in Computed Tomography", Journal of X-Ray science and Technology, vol. No. 21, Issue No. 2, pp. 193-226, 2013.

Office Action issued in connection with corresponding CN Application No. 201410428793.7 dated Oct. 19, 2017.

\* cited by examiner

METHOD FOR REMOVING STREAK FROM DETECTOR CELL WITH PERFORMANCE DIFFERENCE

TECHNICAL FIELD

Embodiments of the present invention generally relate to a computer image processing field, particularly to a method for removing streak from detector cell with performance difference.

BACKGROUND

A computed tomography (CT) is a common endoscopy detection technology in the modern medicine. The CT technology obtains an image of a detected region of a human body by mainly rotating X-ray beams and a detector around the human body, and continuously carrying out section scanning, receiving attenuated X-ray information penetrating the human body by the detector and inputting said information into a computer, reconstructing an image through the computer based on the received attenuated X-ray information during each scanning.

The image reconstruction in the CT technology is an important factor that would affect the detection result. How to clearly and accurately reproduce an image of the detected region is a problem that has always been studied by the person skilled in the art.

From an imaging principle of a CT system, there are multiple factors that would affect a quality of a CT image. For example, in the existing CT system, due to reasons on the structure and manufacturing process of the detector itself, there would inevitably be some performance difference between detector cells on the detector, i.e., there would be some detector cells with performance difference. Projections sensed by those detector cells with performance difference cannot accurately reflect the image of the detected region, thus cannot be applied to the CT image reconstruction directly.

An existing processing method is: in the case that the detector cells with performance difference are determined to be present, usually by an interpolation method, a projection on the detector cell with performance difference is estimated from projections sensed on two detector cells adjacent to the detector cell with performance difference. However, there would be some estimation error between a correct projection of the detector cell with performance difference and the estimated projection. Therefore, during the CT image reconstruction, when an image is reconstructed with projections using a filter backprojection method, the estimation error will be back-projected onto the reconstructed image, thereby forming a streak on the reconstructed image, thus affecting the quality of the CT reconstructed image.

Accordingly, it is necessary to provide an improved method for solving at least one of the technical problems as mentioned above.

BRIEF DESCRIPTION

One aspect of the present invention is to provide a method for removing streaks from detector cells with performance difference, the method comprising the steps of: estimating a projection on a detector cell with performance difference for each of one or more views; reconstructing one or more initial images with the estimated projection on the detector cell with performance difference for each view; estimating a projection error on the detector cell with performance difference for each view from the reconstructed one or more initial images having streaks; and reconstructing one or more output images with the estimated projection error on the detector cell with performance difference for each view to remove the streaks from the reconstructed one or more output images.

In one embodiment of the present invention, in the method as mentioned above, the step of estimating a projection on a detector cell comprises estimating a projection on a detector cell with performance difference using an interpolation method.

In the method as mentioned above, the step of reconstructing one or more output images comprises: subtracting the estimated projection error on the detector cell with performance difference from the estimated projection on the detector cell with performance difference to obtain a corrected projection on the detector cell with performance difference; and reconstructing one or more output images with the corrected projection on the detector cell with performance difference.

In one embodiment of the present invention, in the method as mentioned above, the step of reconstructing one or more initial images comprises reconstructing one or more initial images with the estimated projection on the detector cell with performance difference using a filter backprojection method, and the step of reconstructing one or more output images comprises reconstructing one or more output images with the estimated projection error on the detector cell with performance difference error using a filter backprojection method.

In one embodiment of the present invention, in the method as mentioned above, the step of estimating a projection error on the detector cell comprises: extracting an image stripe along a projection ray of the detector cell with performance difference from the reconstructed one or more initial images; and estimating the projection error on the detector cell with performance difference using one or more gray values of one or more pixels in the extracted image stripe.

In one embodiment of the present invention, in the method as mentioned above, the step of estimating a projection error on the detector cell further comprises: forming a first straight line between a position of an X-ray source and a position of the detector cell with performance difference; selecting second and third straight lines parallel to the first straight line, wherein a distance from the second straight line to the first straight line is the same as a distance from the third straight line to the first straight line; and estimating the projection error on the detector cell with performance difference using one or more gray values of one or more corresponding pixels of the first, the second and the third straight lines.

In one embodiment of the present invention, in the method as mentioned above, the step of estimating a projection error on the detector cell further comprises: dividing the first straight line into M segments; dividing respectively the second and the third straight lines into corresponding M segments as well; and computing the projection error on the detector cell with performance difference using the following equation:

$$p_e(n, \text{row}, \text{view}) = e^{-\left(\frac{a}{M}\right)^2} C_1 \sum_{k=1}^{M} \frac{I_s(k, 2) - \frac{I_s(k, 1) + I_s(k, 3)}{2}}{M}$$

wherein $p_e(n, \text{row}, \text{view})$ represents the projection error on the detector cell with performance difference, $I_s(k,2)$ represents a gray value of the $k^{th}$ segment on the first straight line, $I_s(k,1)$ represents a gray value of the $k^{th}$ segment on the second straight line, $I_s(k,3)$ represents a gray value of the $k^{th}$ segment on the third straight line, M represents the number of the segments divided, $C_1$ represents a constant mapping a streak level to the projection error on the detector cell with performance difference, and a represents the number of non-zero elements $$I_s(\bar{k}, 2) = I_s(k, 2) - \frac{I_s(k, 1) + I_s(k, 3)}{2}, k = [1, M].$$

in $I_s(\bar{k}, 2)$, wherein

In one embodiment of the present invention, in the method as mentioned above, the step of estimating a projection error on the detector cell further comprises: determining whether the $k^{th}$ segment on individual of the first, the second and the third straight lines is in a pixel range of the reconstructed one or more initial images; when it is determined that the $k^{th}$ segment on individual of the first, the second and the third straight lines is not in the pixel range of the reconstructed one or more initial images, the gray value of the $k^{th}$ segment on individual of the first, the second and the third straight lines is zero; and when it is determined that the $k^{th}$ segment on individual of the first, the second and the third straight lines is in the pixel range of the reconstructed one or more initial images, the gray value of the $k^{th}$ segment on individual of the first, the second and the third straight lines is interpolated from the reconstructed one or more initial images.

In one embodiment of the present invention, in the method as mentioned above, the distance from the second straight line to the first straight line and the distance from the third straight line to the first straight line are determined by a size of a detector cell of a detector, a distance from the X-ray source to the detector, a distance from the X-ray source to a rotating center of the X-ray source and a reconstruction kernel.

The method for removing streaks from detector cells with performance difference in accordance with the above embodiments of the present invention can reduce an estimation error by estimating a projection error on the detector cell with performance difference from the reconstructed one or more initial images having streaks, subtracting the estimated projection error on the detector cell with performance difference from the estimated projection on the detector cell with performance difference to further obtain a corrected projection on the detector cell with performance difference, and can remove the streaks from the reconstructed one or more output images by reconstructing one or more output images with the corrected projection on the detector cell with performance difference, improving quality of CT reconstructed images.

Another aspect of the present invention is to provide a method for removing streaks from detector cells with performance difference, the method comprising the steps of: estimating a projection on a detector cell with performance difference for each of one or more views; reconstructing one or more initial images with the estimated projection on the detector cell with performance difference for each view; computing a possible streak direction for each of one or more pixels in the reconstructed one or more initial images; identifying a streak feature for each pixel along the possible streak direction; when identifying a pixel is a streak pixel, smoothing the streak pixel in the streak direction so as to smooth a difference image; and updating one or more output images with the smoothed difference image.

In one embodiment of the present invention, in the method as mentioned above, the step of computing a possible streak direction comprises: forming a first straight line by an X-ray source and each of one or more pixels in the reconstructed one or more initial images; and defining the possible streak direction for each of one or more pixels in the reconstructed one or more initial images by the first straight line.

In one embodiment of the present invention, in the method as mentioned above, the step of identifying a streak feature comprises: selecting several pixel points near the pixel along the possible streak direction in the reconstructed one or more initial images; selecting a second straight line passing each of the several pixel points and perpendicular to the possible streak direction; for each of the several pixel points, finding two pixel points adjacent to the pixel point in the second straight line; comparing a gray value of the pixel point to gray values of its adjacent two pixel points; and identifying a streak feature for the pixel using the compared result.

In one embodiment of the present invention, in the method as mentioned above, the step of identifying a steak feature further comprises: if the gray value of the pixel point is always smaller than the gray values of its adjacent two pixel points for each of the several pixel points, regarding the pixel as a streak pixel; or if the gray value of the pixel point is always bigger than the gray values of its adjacent two pixel points for each of the several pixel points, regarding the pixel as a streak pixel.

In one embodiment of the present invention, in the method as mentioned above, the step of smoothing the streak pixel comprises:

smoothing the streak pixel in the streak direction using the following equation:

$$\tilde{I}(i,j) = w1 \times I1 + w2 \times I(i,j) + w3 \times I2$$

wherein w1, w2 and w3 represent weighting factors, each of the reconstructed one or more initial images is an N×N image, $I(i,j)$ represents a gray value of the streak pixel $P(i,j)$, $i,j=[0, N]$ I1 and I2 respectively represent gray values of the two pixels adjacent to the streak pixel $P(i,j)$ in a second straight line passing the streak pixel $P(i,j)$ and perpendicular to the streak direction, and $\tilde{I}(i,j)$ represents a correct gray value of the streak pixel $P(i,j)$.

In one embodiment of the present invention, in the method as mentioned above, the step of updating one or more output images comprises: obtaining an output image using the following equation:

$$I_o = I + C_2 \times \text{smooth}(\tilde{I} - I)$$

wherein $I_o$ represents an output image, I represents a reconstructed initial image, $\tilde{I}$ represents a corrected image obtained from $\tilde{I}(i,j)$, smooth represents a smooth operator and $C_2$ represents a parameter for mapping a difference level to $(\tilde{I}-I)$ after the smooth operator.

The method for removing streaks from detector cells with performance difference in accordance with the above embodiments of the present invention can remove the streaks from the reconstructed one or more initial images directly by identifying pixels in the streak direction from the reconstructed one or more initial images having streaks and smoothing the streak pixels, thus improving quality of CT reconstructed images.

A further aspect of the present invention is to provide a method for removing streaks from detector cells with performance difference, the method comprising the steps of: estimating a projection on a detector cell with performance difference for each of one or more views when an X-ray source is located in each of one or more positions; estimating a projection error on a conjugate detector cell for a conjugate view when the X-ray source is located in a conjugate position relative to each position, wherein each position and its conjugate position are located in a connecting line between the X-ray source and the detector cell with performance difference when the X-ray source is located in the each position; and reconstructing one or more output images using the estimated projection on the detector cell with performance difference and the estimated projection error on the conjugate detector cell.

In one embodiment of the present invention, in the method as mentioned above, the step of estimating a projection on a detector cell comprises: computing projections on detector cells adjacent to the detector cell with performance difference; and estimating a projection on the detector cell with performance difference with the computed projections on the detector cells adjacent to the detector cell with performance difference using an interpolation method.

In one embodiment of the present invention, in the method as mentioned above, the step of estimating a projection error on a conjugate detector cell comprises: computing a conjugate projection $P_{c0}$ on the conjugate detector cell for a conjugate view when the X-ray source is located in a conjugate position relative to each position; estimating a conjugate projection $P_c$ on the conjugate detector cell for the conjugate view when the X-ray source is located in the conjugate position relative to each position; and subtracting the computed conjugate projection from the estimated conjugate projection to estimate the projection error, $P_c - P_{c0}$ on the conjugate detector cell.

In one embodiment of the present invention, in the method as mentioned above, the step of estimating a conjugate projection $P_C$ further comprises: computing projections on detector cells adjacent to the conjugate detector cell; and estimating a conjugate projection on the conjugate detector cell with the computed projections on the detector cells adjacent to the conjugate detector cell using an interpolation method.

In one embodiment of the present invention, in the method as mentioned above, the step of reconstructing one or more output images comprises: subtracting the estimated projection error on the conjugate detector cell from the estimated projection on the detector cell with performance difference to obtain an improved projection; and reconstructing one or more output images with the improved projection.

The method for removing streaks from detector cells with performance difference in accordance with the above embodiments of the present invention can remove the streaks from detector cells with performance difference from the reconstructed one or more output images by utilizing a conjugate projection ray of the X-ray source and utilizing a conjugate projection ray sensed by a conjugate detector cell to the detector cell with performance difference, estimating an estimation error that is possible to occur on the detector cell with performance difference with a projection error that is possible to occur on the conjugate detector cell, reducing the estimation error caused by low sampling of the detector cell with performance difference, and reconstructing one or more output images with the improved projection, thus improving quality of CT reconstructed images.

BRIEF DESCRIPTION OF THE DRAWINGS

These and other features, aspects and advantages of the present invention can be better understood when the following detailed description is read with reference to the accompanying drawings, in which the same reference signs represent the same components in the whole drawings, in which.

DETAILED DESCRIPTION

In order to help the person skilled in the art to exactly understand the subject matters claimed by the present disclosure, embodiments of the present invention will be described in detail hereinafter with reference to the accompanying drawings. In the following detailed description for those embodiments, some known functions or structures will not be described in detail in the Description, to avoid disclosure to be affected by unnecessary details.

Unless defined otherwise, the technical or scientific terms used in the Claims and the Description should have meanings as commonly understood by one of ordinary skilled in the art to which the present disclosure belongs. The terms "first," "second" and the like in the Description and the Claims do not mean any sequential order, quantity or importance, but are only used for distinguishing different components. The terms "a," "an" and the like do not denote a limitation of quantity, but denote the existence of at least one. The terms "comprises," "comprising," "includes," "including" and the like mean that the element or object in front of the "comprises," "comprising," "includes" and "including" covers the elements or objects and their equivalents illustrated following the "comprises," "comprising," "includes" and "including," but do not exclude other elements or objects. The term "coupled" or "connected" or the like is not limited to being connected physically or mechanically, but may comprise electric connection, no matter directly or indirectly.

Figure 1:
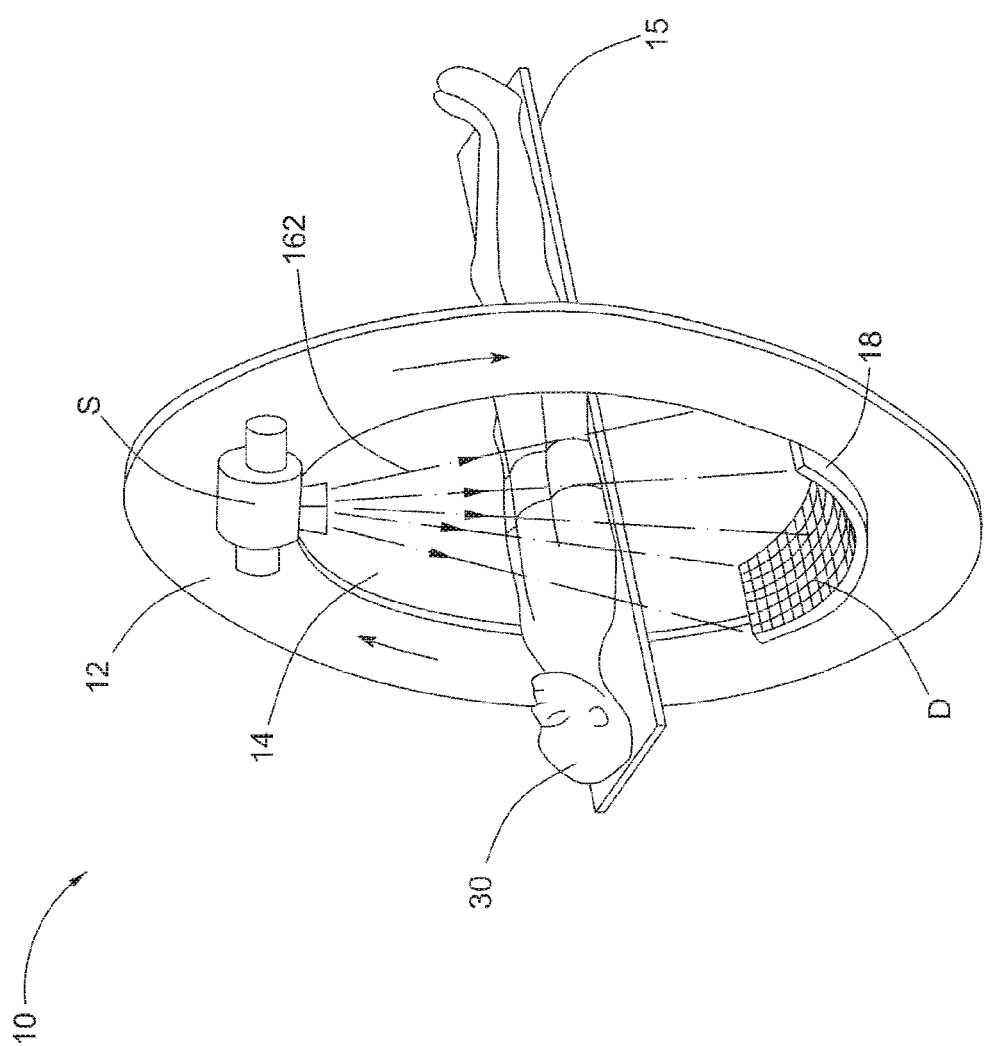
FIG. 1 is a schematic diagram of one type of CT system when detecting a patient.

FIG. 1 illustrates a schematic diagram of one type of CT system when detecting a patient. As shown in FIG. 1, the CT system 10 generally comprises a rotatable gantry 12 and a supporting table 15 disposed in a hollow imaging area 14 in the rotatable gantry 12 for supporting a patient 30. The rotatable gantry 12 includes an X-ray source S and a detector 18 disposed opposite to the X-ray source S, in which the detector 18 includes a plurality of independent detector cells D arranged in an array. When the rotatable gantry 12 is located in a certain scanning position, the X-ray source S emits a sector-shaped beam of X-rays 162 towards a direction of the detector 18, and the plurality of detector cells D sense the X-rays attenuated through the patient 30 respectively, thus a set of projections are sensed by the detector cells D to obtain a corresponding view. As the rotatable gantry 12 rotates, the X-ray source S and the detector 18 rotate along with it around a rotating center O. The CT system 10 carries out a plurality of scans. During each of the plurality of scans, each corresponding view may be sensed by all the detector cells D. In the case that the detector cells D are normal, one or more images may be reconstructed directly using each corresponding view. However, when there is some performance difference between the detector cells D on the detector 18, i.e., in the case that the detector 18 has a detector cell D(n,row) with performance difference (in which n is a column number of the detector cell D(n,row) with performance difference in the array of the detector 18, row is a row number of the detector cell D(n,row) with performance difference in the array of the detector 18), the projection for each view sensed by the detector cell D(n,row) with performance difference cannot correctly reflect soft tissue features of the patient 30, therefore, the projection for each view sensed by the detector cell D(n,row) with performance difference cannot be used. It is needed to estimate a projection on the detector cell D(n,row) with performance difference for each view as accurately as possible by the following method.

Figure 2:
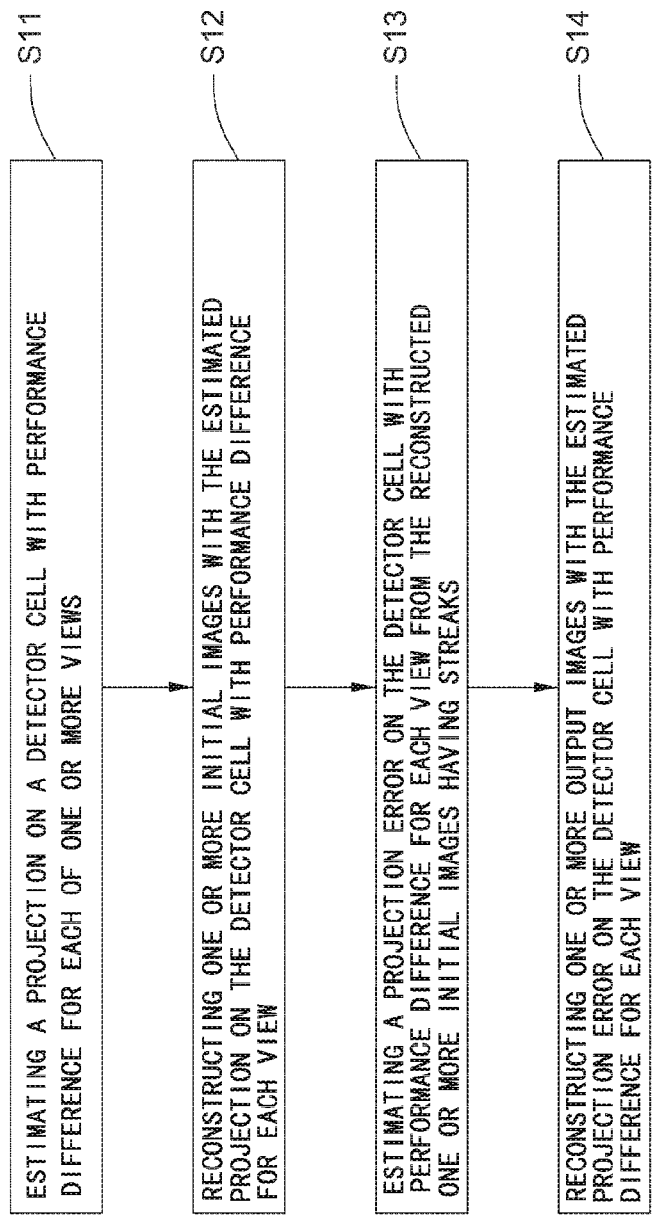
FIG. 2 is a flow chart of a method for removing streaks from detector cells with performance difference in accordance with a first embodiment of the present invention.

FIG. 2 illustrates a flow chart of a method for removing streaks from detector cells with performance difference in accordance with a first embodiment of the present invention. Now referring to FIG. 2, the method for removing streaks from detector cells with performance difference in accordance with a first embodiment of the present invention comprises the following steps:

In Step s11, a projection P(n,row,view) on a detector cell D(n,row) with performance difference for each of one or more views is estimated, in which n is a column number of the detector cell D(n,row) with performance difference, row is a row number of the detector cell D(n,row) with performance difference, view is a view number of the projection. In the present embodiment, the projection P(n,row,view) on the detector cell D(n,row) with performance difference may be estimated using a known interpolation method. The known interpolation method may be any suitable interpolation method. For example, the projection P(n,row,view) on the detector cell with performance difference is estimated with the projections measured on two detector cells adjacent to the detector cell D(n,row) with performance difference by a known interpolation method.

In Step s12, one or more initial images I are reconstructed with the projection P(n,row,view) on the detector cell with performance difference for each view estimated through Step s11. In the present embodiment, one or more initial images I may be reconstructed with the estimated projection P(n,row,view) on the detector cell with performance difference using a filter backprojection method. Since there is an estimation error δ(i,row,view) between the estimated projection P(n,row,view) of the detector cell D(n,row) with performance difference in Step s11 and a correct projection of the detector cell D(n,row) with performance difference, there exist streaks in the one or more initial images I reconstructed in Step s12, and the estimation error δ(i,row,view) is just the reason that causes the existence of streaks on the reconstructed one or more initial images I. Therefore, if the estimation error δ(i,row,view) can be reduced to a very small value, even approaching zero, then the streaks on the reconstructed one or more initial images I can be removed. Accordingly, the following steps are just to attempt to reduce the estimation error δ(i,row,view), so as to remove the streaks on the reconstructed one or more initial images I.

In Step s13, a projection error $p_e$(n,row,view) on the detector cell with performance difference for each view is estimated from the reconstructed one or more initial images I having streaks.

In one embodiment of the present invention, Step s13 comprises: Step s131, extracting an image stripe along a projection ray of the detector cell D(n,row) with performance difference from the reconstructed one or more initial images I; and Step s132, estimating the projection error $p_e$(n,row,view) on the detector cell with performance difference using one or more gray values of one or more pixels in the extracted image stripe.

Figure 3:
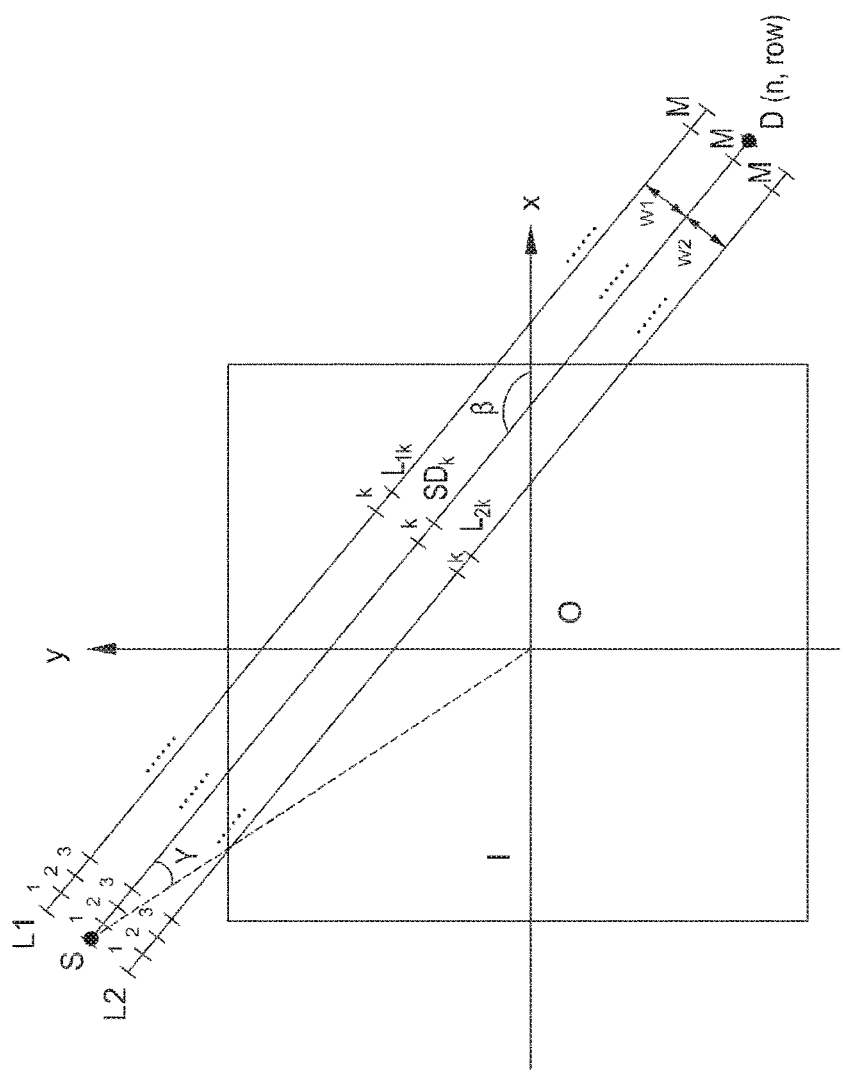
FIG. 3 is a schematic diagram used by the method as shown in FIG. 2 when estimating a projection error on a detector cell with performance difference.

Referring to FIG. 3, a first straight line SD is formed between the position of the X-ray source S and the position of the detector cell D(n,row) with performance difference. Two straight lines parallel to the first straight line SD are selected at two sides respectively adjacent to the first straight line SD, which are referred to as a second straight line L1 and a third straight line L2 respectively, and a distance w1 from the second straight line L1 to the first straight line SD is equal to a distance w2 from the third straight line L2 to the first straight line SD. Specifically, the distance w1 from the second straight line L1 to the first straight line SD and the distance w2 from the third straight line L2 to the first straight line SD are determined by a size of a detector cell D of the detector 18, a distance from the X-ray source S to the detector 18, a distance from the X-ray source S to the rotating center O of the X-ray source S and a reconstruction convolution kernel.

Specifically, Step s132 further comprises estimating the projection error $p_e$(n,row,view) on the detector cell with performance difference using one or more gray values of one or more corresponding pixels of the first, the second and the third straight lines SD, L1 and L2.

Continuing to refer to FIG. 3, first, the first straight line SD is divided into M segments, in which $SD_k$ in FIG. 3 represents the $k^{th}$ segment on the first straight line SD. Then, the second straight line L1 and the third straight line L2 are respectively divided into corresponding M segments as well, in which $L_{1k}$ in FIG. 3 represents the $k^{th}$ segment on the second straight line L1, and $L_{2k}$ in FIG. 3 represents the $k^{th}$ segment on the third straight line L2.

The projection error $p_e$(n,row,view) on the detector cell with performance difference may be calculated using the following equation:

$$p_e(n, \text{row}, \text{view}) = e^{-\left(\frac{a}{M}\right)^2} C_1 \sum_{k=1}^{M} \frac{I_s(k, 2) - \frac{I_s(k, 1) + I_s(k, 3)}{2}}{M} \quad (1)$$

$$I_s(\overline{k}, 2) = I_s(k, 2) - \frac{I_s(k, 1) + I_s(k, 3)}{2}, k = [1, M] \quad (2)$$

wherein $I_s(k,2)$ represents a gray value of the $k^{th}$ segment $SD_k$ on the first straight line SD, $I_s(k,1)$ represents a gray value of the $k^{th}$ segment $L_{1k}$ on the second straight line L1, $I_s(k,3)$ represents a gray value of the $k^{th}$ segment $L_{2k}$ on the third straight line L2. First, it is needed to determine whether the $k^{th}$ segments, $SD_k$, $L_{1k}$ and $L_{2k}$ on individual of the first, the second and the third straight lines SD, L1 and L2 are in a pixel range of the reconstructed one or more initial images I, wherein the individual positions may be determined based on a distance from the X-ray source S to the detector cell D(n,row) with performance difference, a fan angle γ (an angle between the connecting line SD from the X-ray source S to the detector cell D(n,row) with performance difference and a connecting line SO from the X-ray source S to its rotating center O) of the X-ray source S and a projection angle β (an angle between the connecting line SD from the X-ray source S to the detector cell D(n,row) with performance difference and a horizontal x-axis) of the X-ray source S. If it is determined that the VI segments, $SD_k$, $L_{1k}$ and $L_{2k}$ on individual of the first, the second and the third straight lines SD, L1 and L2 are within the pixel range of the reconstructed one or more initial images I, the gray values $I_s(k,2)$, $I_s(k,1)$ and $I_s(k,3)$ of the $k^{th}$ segments, $SD_k$, $L_{1k}$ and $L_{2k}$ on individual of the first, the second and the third straight lines SD, L1 and L2 may be interpolated from the reconstructed one or more initial images I based on the individual positions; if it is determined that the $k^{th}$ segments, $SD_k$, $L_{1k}$ and $L_{2k}$ on individual of the first, the second and the third straight lines SD, L1 and L2 are not within the pixel range of the reconstructed one or more initial images I, the gray values $I_s(k,2)$, $I_s(k,1)$ and $I_s(k,3)$ of the $k^{th}$ segments $SD_k$, $L_{1k}$ and $L_{2k}$ on individual of the first, the second and the third straight lines SD, L1 and L2 are equal to zero.

In addition, M represents the number of the segments divided, a represents the number of non-zero elements in $I_s(\overline{K}, 2)$ in Equation (2), $C_1$ represents a constant mapping a streak level to the projection error on the detector cell with performance difference.

In Step s14, one or more output images $I_o$ are reconstructed with the estimated projection error $p_e(n,row,view)$ on the detector cell with performance difference for each view, to remove the streaks from the reconstructed one or more output images $I_o$. In the present embodiment, one or more output images $I_o$ are reconstructed with the estimated projection error $p_e(n,row,view)$ on the detector cell with performance difference using a filter backprojection method.

Furthermore, Step s14 comprises: Step s141, subtracting the estimated projection error $p_e(n,row,view)$ on the detector cell with performance difference from the estimated projection P(n,row,view) on the detector cell with performance difference to obtain a corrected projection $\tilde{P}(n,row,view)$ on the detector cell with performance difference, i.e., as shown in the following equation:

$$\tilde{P}(n,row,view)=P(n,row,view)-p_e(n,row,view) \quad (3)$$

Step s142, reconstructing one or more output images $I_o$ with the corrected projection $\tilde{P}(n,row,view)$ on the detector cell with performance difference obtained through Step s141.

The method for removing streaks from detector cells with performance difference of the first embodiment of the present invention can reduce an estimation error by estimating a projection error $p_e(n,row,view)$ on the detector cell with performance difference from the reconstructed one or more initial images I having streaks, subtracting the estimated projection error $p_e(n,row,view)$ on the detector cell with performance difference from the estimated projection P(n, row,view) on the detector cell with performance difference to further obtain a corrected projection $\tilde{P}(n,row,view)$ on the detector cell with performance difference, and can remove the streaks from the reconstructed one or more output images $I_o$ by reconstructing one or more output images $I_o$ with the corrected projection $\tilde{P}(n,row,view)$ on the detector cell with performance difference, improving quality of CT reconstructed images.

Figure 4:
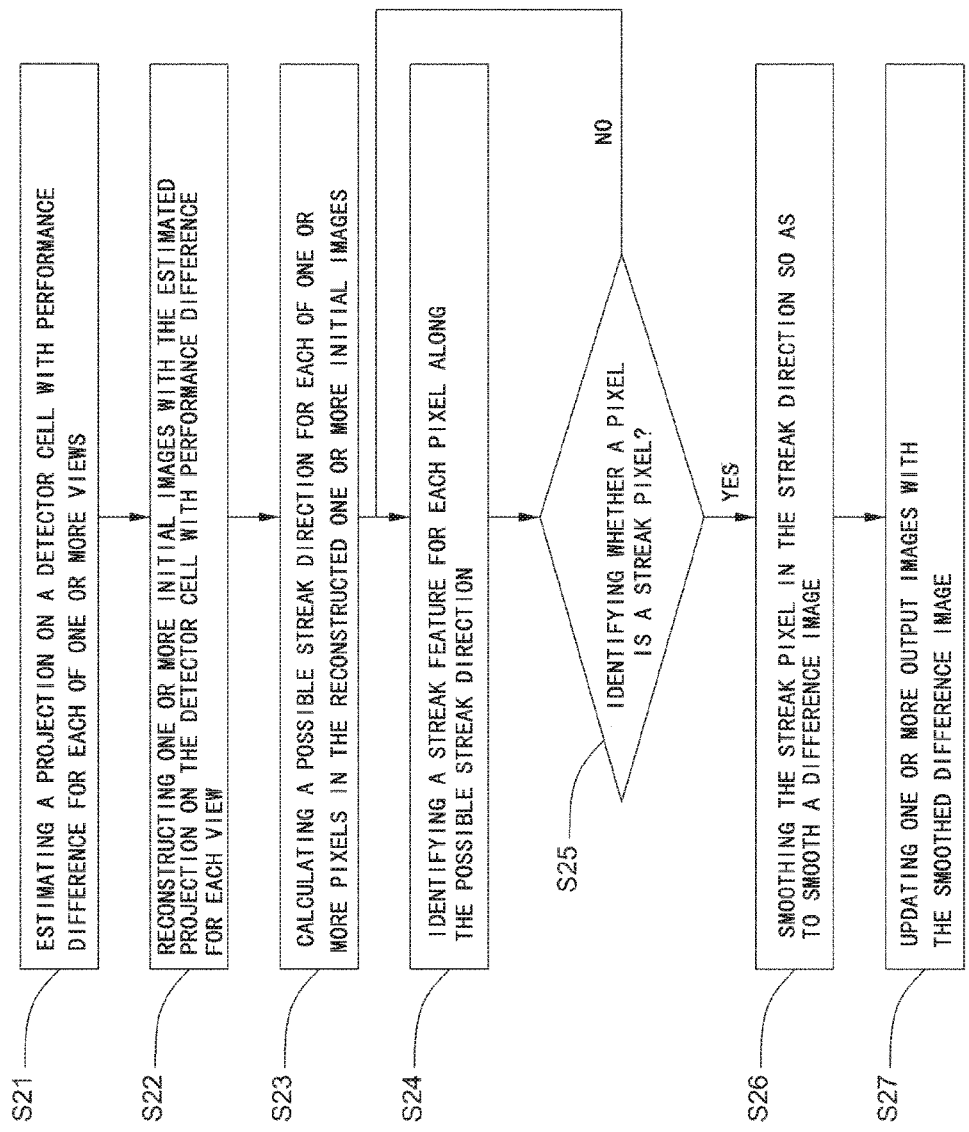
FIG. 4 is a flow chart of a method for removing streaks from detector cells with performance difference in accordance with a second embodiment of the present invention.

FIG. 4 illustrates a flow chart of a method for removing streaks from detector cells with performance difference in accordance with a second embodiment of the present invention. Now referring to FIG. 4, the method for removing streaks from detector cells with performance difference in accordance with a second embodiment of the present invention comprises the following steps:

In Step s21, a projection P(n,row,view) on a detector cell D(n,row) with performance difference for each of one or more views is estimated, in which n is a column number of the detector cell D(n,row) with performance difference, row is a row number of the detector cell D(n,row) with performance difference, view is a view number of the projection. In the present embodiment, the projection P(n,row,view) on the detector cell D(n,row) with performance difference may be estimated using a known interpolation method. The known interpolation method may be any suitable interpolation method. For example, the projection P(n,row,view) on the detector cell with performance difference is estimated with the projections sensed on two detector cells adjacent to the detector cell D(n,row) with performance difference by a known interpolation method.

In Step s22, one or more initial images I are reconstructed with the projection P(n,row,view) on the detector cell with performance difference for each view estimated through Step s11, each of the reconstructed one or more initial images I being an N×N image. In the present embodiment, one or more initial images I may be reconstructed with the estimated projection P(n,row,view) on the detector cell with performance difference using a filter backprojection method. Since there is an estimation error δ(i,row,view) between the estimated projection P(n,row,view) of the detector cell D(n, row) with performance difference in Step s21 and a correct projection of the detector cell D(n,row) with performance difference, there exist streaks in the reconstructed one or more initial images I in Step s22. The streaks present on the reconstructed one or more initial images I are generally distributed along a straight line, while there is very little straight line structure in images of a human tissue. Therefore, if a straight line structure can be identified from the reconstructed one or more initial images I and pixels on said straight line can be smoothed, then streaks can be removed from the reconstructed one or more initial images I. Accordingly, the following steps are to remove the streaks on the reconstructed one or more initial images I in light of such ideas.

In Step s23, a possible streak direction for each of one or more pixels in the reconstructed one or more initial images I is calculated.

Figure 5:
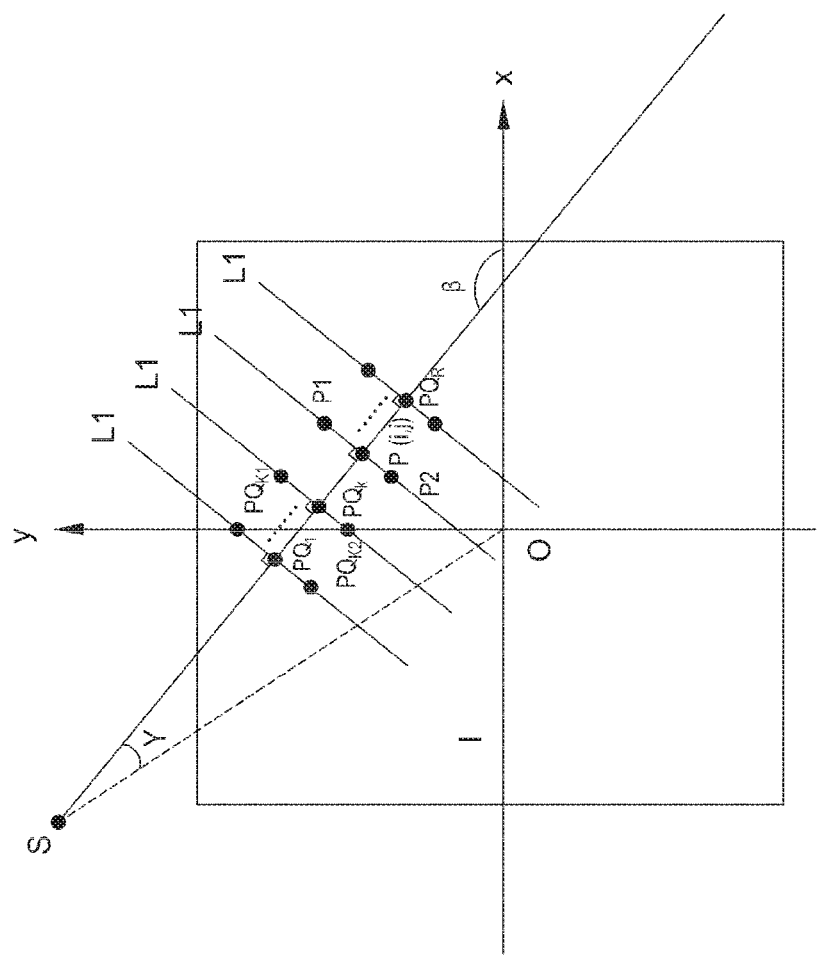
FIG. 5 is a schematic diagram used by the method as shown in FIG. 4 when estimating a possible streak direction.

Referring to FIG. 5, the position of the X-ray source S and each pixel P(i,j) of one or more pixels in the reconstructed one or more initial images I form a first straight line SP, wherein i=[0, N], j=[0, N].

The first straight line SP defines the possible streak direction for each pixel P(i,j) of one or more pixels in the reconstructed one or more initial images I, i.e., the possible streak direction is a direction along the first straight line SP.

In Step s24, a streak feature for each pixel P(i,j) along the possible streak direction SP is identified.

Continuing to refer to FIG. 5, first, several pixel points $PQ_1, \ldots, PQ_R$ adjacent to the pixel P(i,j) are selected along the possible streak direction SP in the reconstructed one or more initial images I.

A straight line is selected to pass each pixel point $PQ_k$ (k=[1, R]) of the several pixel points and perpendicular to the possible streak direction SP, which is referred to as a second straight line L1.

For each pixel point $PQ_k$ of the several pixel points, find two pixel points $PQ_{k1}$, $PQ_{k2}$ adjacent to the pixel point $PQ_k$ in the second straight line L1, compare a gray value of the pixel point $PQ_k$ to gray values of its adjacent two pixel points $PQ_{k1}$, $PQ_{k2}$, and identify a streak feature for the pixel P(i,j) using the compared results.

In Step s25, identify whether a pixel P(i,j) is a streak pixel. In the case of identifying that the pixel P(i,j) is a streak pixel, the process proceeds to Step s25; in the case of identifying that the pixel P(i,j) is not a streak pixel, the process returns back to Step s24.

In one embodiment of the present invention, if there is always the gray value of the pixel point $PQ_k$ that is smaller than the gray values of its adjacent two pixel points $PQ_{k1}$, $PQ_{k2}$ for each pixel point $PQ_k$, k=[1, R] of the several pixel points, the pixel P(i,j) is regarded as a streak pixel. Or, alternatively, in another embodiment of the present invention, if there is always the gray value of the pixel point $PQ_k$ that is bigger than the gray values of its adjacent two pixel points $PQ_{k1}$, $PQ_{k2}$ for each pixel point $PQ_k$, k−[1, R] of the several pixel points, the pixel P(i,j) is regarded as a streak pixel.

In Step s26, when a pixel P(i,j) is identified as a streak pixel, the streak pixel P(i,j) in the streak direction is smoothed so as to smooth a difference image.

Referring to FIG. 5, similarly, a second straight line L1 is selected in a direction passing the streak pixel P(i,j) and perpendicular to the streak direction SP. Then, two pixels P1, P2 adjacent to the streak pixel P(i,j) are found in the second straight line L1.

In one embodiment of the present invention, in Step s26, the steak pixel P(i,j) in the streak direction is smoothed using the following equation:

$$\tilde{I}(i,j) = w1 \times I1 + w2 \times I(i,j) + w3 \times I2 \quad (4)$$

wherein w1, w2 and w3 represent weighting factors, I(i,j) represents a gray value of the streak pixel P(i,j), I1 and I2 respectively represent gray values of the two pixels P1, P2 adjacent to the streak pixel P(i,j), and $\tilde{I}(i,j)$ represents a correct gray value of the streak pixel P(i,j).

The positions of each pixel point $PQ_k$ and its adjacent two pixel points $PQ_{k1}$, $PQ_{k2}$ and two pixels P1, P2 adjacent to the streak pixel P(i,j) may be determined based on a distance from the X-ray source S to the streak pixel P(i,j), a fan angle γ (an angle between the connecting line SP from the X-ray source S to the streak pixel P(i,j) and the connecting line SO from the X-ray source S to its rotating center O) of the X-ray source S and a projection angle β (an angle between the connecting line SP from the X-ray source S to the streak pixel P(i,j) and the positive direction of the horizontal x-axis) of the X-ray source S and the like. The individual gray values may be determined based on the individual positions in the reconstructed one or more initial images I.

A difference image $I_D$ is obtained by the following equation:

$$I_D = \tilde{I} - I \quad (5)$$

wherein I represents a reconstructed initial image, $\tilde{I}$ represents a corrected image obtained from $\tilde{I}(i,j)$.

After obtaining the difference image $I_D$, the difference image $I_D$ is smoothed to remove a high-frequency component from the difference image $I_D$.

In Step s27, one or more output images $I_o$ are updated with the smoothed difference image, such that the output images $I_o$ will become more natural, without flicker.

In one embodiment of the present invention, the output image $I_o$ is obtained using the following equation:

$$I_o = I + C_2 \times \text{smooth}(\tilde{I} - I) \quad (6)$$

wherein smooth represents a smooth operator and $C_2$ represents a parameter for mapping a difference level to the difference image $(\tilde{I} - I)$ after the smooth operator.

The method for removing streaks from detector cells with performance difference of the second embodiment of the present invention can remove the streaks from the reconstructed one or more initial images I directly by identifying pixels in the streak direction from the reconstructed one or more initial images I having streaks and smoothing the streak pixels, thus improving quality of CT reconstructed images.

The projections on the detector cells D(n,row) with performance difference may be estimated using the projections on the adjacent detector cells by a known interpolation method. However, tiny structures in the human body may cause a larger estimation error, which cannot be reduced by an advanced interpolation method. Therefore, embodiments of the present invention provide a method for removing streaks from detector cells with performance difference of the third embodiment. The reason for causing said estimation error is a low sampling rate due to the detector cell D(n,row) with performance difference. In the present method, the estimation error may be reduced using redundant information from a sine diagram. Since the conjugate projection ray of the X-ray source S is most likely to pass similar tiny structures, and since a taper angle of the beam 162 of X-rays cannot use a conjugate projection of the conjugate projection ray directly, the present method utilizes a high sampling rate of a conjugate detector cell at a conjugate position to generate correct date, thereby obtaining the estimation error caused by the low sampling rate of the detector cell D(n,row) with performance difference by an interpolation method. The method for removing streaks from detector cells with performance difference of the third embodiment of the present invention is described in detail in the following.

Figure 6:
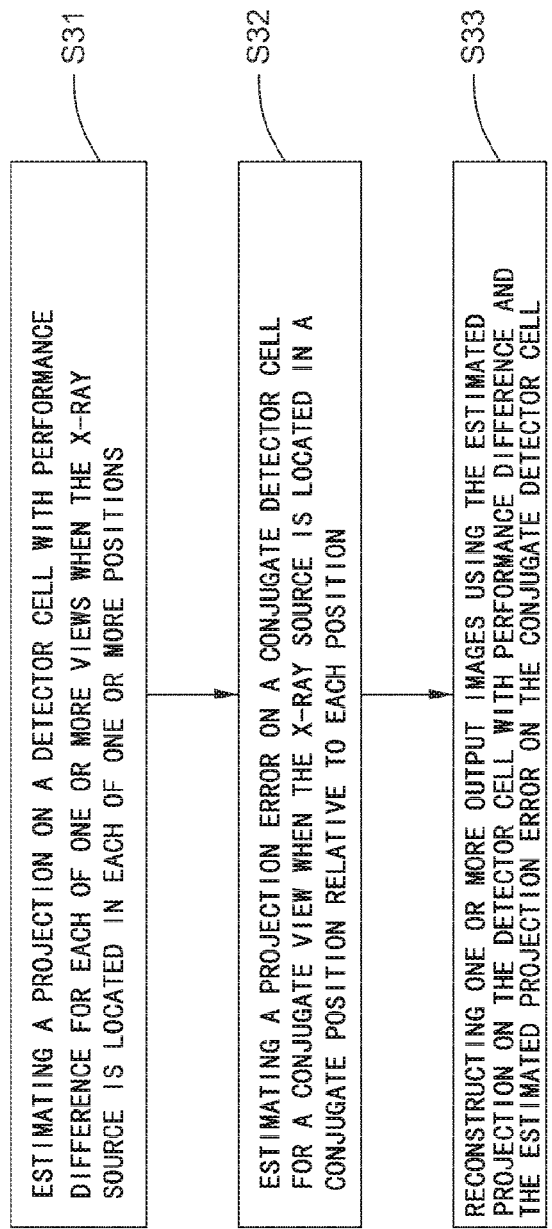
FIG. 6 is a flow chart of a method for removing streaks from detector cells with performance difference in accordance with a third embodiment of the present invention.

FIG. 6 illustrates a flow chart of the method for removing streaks from detector cells with performance difference in accordance with the third embodiment of the present invention. Now referring to FIG. 6, the method for removing streaks from detector cells with performance difference in accordance with the third embodiment of the present invention comprises the following steps:

In Step s31, a projection P(n,row,view) on a detector cell D(n,row) with performance difference for each of one or more views when the X-ray source S is located in each of one or more positions is estimated.

Figure 7B:
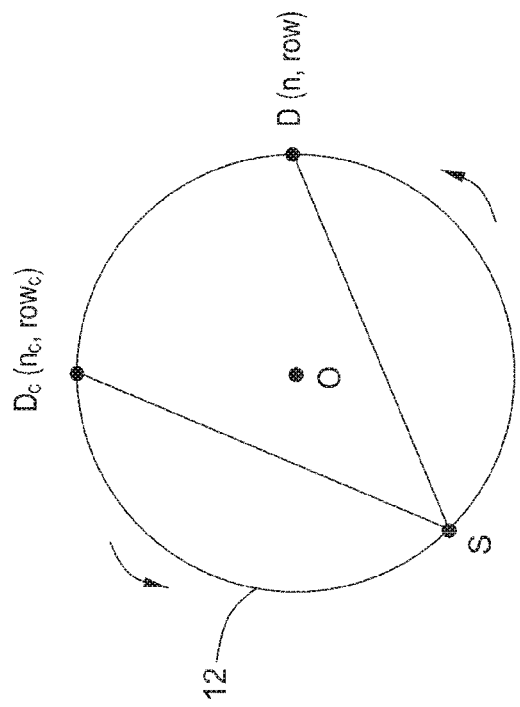
FIG. 7B shows a simplified illustration when the X-ray source is located in a conjugate position of the position as shown in FIG. 7A.
Figure 7A:
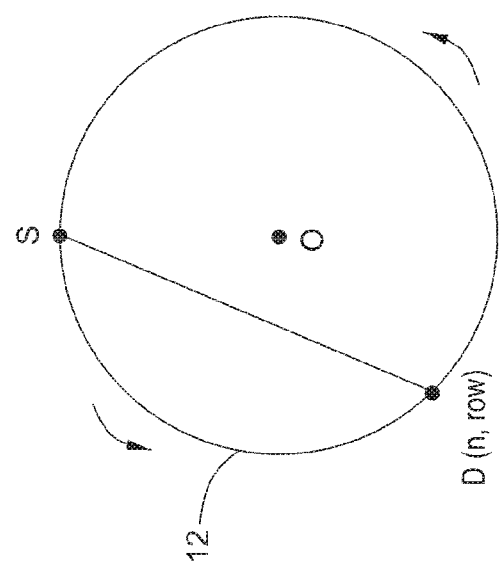
FIG. 7A shows a simplified illustration when an X-ray source is located in one position.

When the rotatable gantry 12 is located in a certain scanning position, the X-ray source S is located in a position as shown in FIG. 7A, in which projections on detector cells adjacent to the detector cell D(n,row) with performance difference may be calculated from the sensed information on the detector cells adjacent to the detector cell D(n,row) with performance difference. In one embodiment of the present invention, by the sensed information on four detector cells adjacent to the detector cell D(n,row) with performance difference, projections P(n−2, $row_{-2}$, view) P(n−1, $row_{-1}$, view) P(n+1, $row_{+1}$, view) and P(n+2, $row_{+2}$, view) on the four detector cells adjacent to the detector cell D(n,row) with performance difference in the position may be calculated respectively. According to different scanning methods, the row numbers $row_{-2}$, $row_{-1}$, $row_{+1}$ and $row_{+2}$ of the adjacent four detector cells may be the same as or different from the row number row of the detector cell D(n,row) with performance difference.

Then, using any suitable known interpolation method, the projection P(n,row,view) on the detector cell D(n,row) with performance difference may be estimated with the calculated projections P(n−2, row$_{-2}$, view), P(n−1, row$_{-1}$, view), P(n+1, row$_{+1}$, view) and P(n+2, row$_{+2}$, view) on the detector cells adjacent to the detector cell D(n,row) with performance difference, i.e., as shown in the following equation:

$$P(n,\text{row},\text{view})=L(P(n-2,\text{row}_{-2},\text{view}),P(n-1,\text{row}_{-1},\text{view}), P(n+1,\text{row}_{+1},\text{view}),P(n+2,\text{row}_{+2},\text{view})) \quad (7)$$

However, embodiments of the present invention are not limited thereto. In another embodiment of the present invention, the projection P(n,row,view) on the detector cell D(n,row) with performance difference may be estimated with the projections on two or more detector cells adjacent to the detector cell D(n,row) with performance difference.

In Step s32, a projection error on a conjugate detector cell for a conjugate view when the X-ray source S is located in a conjugate position relative to each position is estimated, wherein each position and its conjugate position are located in a connecting line between the X-ray source S and the detector cell D(n,row) with performance difference when the X-ray source S is located in each position.

As the rotatable gantry 12 rotates, the X-ray source S and the detector 18 rotate around the rotating center O along with it. When the rotatable gantry 12 rotates to a conjugate position of the position of the X-ray source S as shown in FIG. 7A, i.e., the X-ray source S rotates to be located in the conjugate position as shown in FIG. 7B along with it, i.e., the conjugate position of the X-ray source S as shown in FIG. 7B corresponds to the position of the detector cell D(n,row) with performance difference when in the position of the X-ray source S as shown in FIG. 7A. When in the conjugate position of the X-ray source S as shown in FIG. 7B, the detector cell D(n,row) with performance difference rotates from the position as shown in FIG. 7A to the position as shown in FIG. 7B, and at this moment, the conjugate detector cell of the detector cell D(n,row) with performance difference just corresponds to the position of the X-ray source S as shown in FIG. 7A.

In one embodiment of the present invention, Step s32 comprises:

In Step s321, a conjugate projection $P_{c0}(n_C, \text{row}_c, \text{view}_c)$ on the conjugate detector cell $D_c(n_c, \text{row}_c)$ for a conjugate view when the X-ray source S is located in a conjugate position relative to each position is calculated.

In the conjugate position as shown in FIG. 7B, the conjugate projection rays emitted from the X-ray source S will be sensed by the conjugate detector cell $D_c(n_c, \text{row}_c)$ of the detector cell D(n,row) with performance difference, and the conjugate projection $P_{c0}(n_c, \text{row}_c, \text{view}_c)$ on the conjugate detector cell $D_c(n_c, \text{row}_c)$ may be calculated directly from the sensed information of the conjugate detector cell $D_c(n_c, \text{row}_c)$.

In Step s322, a conjugate projection $P_c(n_c, \text{row}_c, \text{view}_c)$ on the conjugate detector cell $D_c(n_c, \text{row}_c)$ for a conjugate view when the X-ray source S is located in a conjugate position relative to each position is estimated.

When the X-ray source S is in the conjugate position as shown in FIG. 7B, the projections on the detector cells adjacent to the conjugate detector cell D(n,row) may be calculated by the sensed information of the detector cell in the conjugate position corresponding to the detector cells adjacent to the detector cell D(n,row) with performance difference. In one embodiment of the present invention, by the four detector cells adjacent to the conjugate detector cell D(n,row), projections $P_{c0}(n_c-2, \text{row}_{c-2}, \text{view}_c)$, $P_{c0}(n_c-1, \text{row}_{c-1}, \text{view}_c)$, $P_{c0}(n_c+1, \text{row}_{c+1}, \text{view}_c)$ and $P_{c0}(n_c+2, \text{row}_{c+2}, \text{view}_c)$ on the four detector cells adjacent to the conjugate detector cell D(n,row) in the position may be computed respectively. According to different scanning methods, the row numbers $\text{row}_{c-2}$, $\text{row}_{c-1}$, $\text{row}_{c+1}$ and $\text{row}_{c+2}$ of the adjacent four detector cells may be the same as or different from the row number $\text{row}_c$ of the conjugate detector cell $D_c(n_c, \text{row}_c)$.

Then, using any suitable known interpolation method, the conjugate projection $P_c(n_c, \text{row}_c, \text{view}_c)$ on the conjugate detector cell $D_c(n_c, \text{row}_c)$ may be estimated with the computed projections $P_{c0}(n_c-2, \text{row}_{c-2}, \text{view}_c)$, $P_{c0}(n_c-1, \text{row}_{c-1}, \text{view}_c)$, $P_{c0}(n_c+1, \text{row}_{c+1}, \text{view}_c)$ and $P_{c0}(n_c+2, \text{row}_{c+2}, \text{view}_c)$ on the detector cells adjacent to the conjugate detector cell $D_c(n_c, \text{row}_c)$, i.e., as shown in the following equation:

$$P_e(n_e, \text{row}_e, \text{view}_e) = \\ L(P_{e0}(n_e-2, \text{row}_{e-2}, \text{view}_e), P_{e0}(n_e-1, \text{row}_{e-1}, \text{view}_e), \\ P_{e0}(n_e+1, \text{row}_{e+1}, \text{view}_e), P_{e0}(n_e+2, \text{row}_{e+2}, \text{view}_e)) \quad (8)$$

However, embodiments of the present invention are not limited thereto. In another embodiment of the present invention, the conjugate projection $P_c(n_c, \text{row}_c, \text{view}_c)$ on the conjugate detector cell $D_c(n_c, \text{row}_c)$ may be estimated with the projections on two or more detector cells adjacent to the conjugate detector cell $D_c(n_c, \text{row}_c)$ by a known interpolation method.

In Step s323, the computed conjugate projection $P_{c0}(n_c, \text{row}_c, \text{view}_c)$ on the conjugate detector cell $D_c(n_c, \text{row}_c)$ is subtracted from the estimated conjugate projection $P_c(n_c, \text{row}_c, \text{view}_c)$ on the conjugate detector cell $D_c(n_c, \text{row}_c)$ to estimate the projection error $p_{ce}(n,\text{row},\text{view})$ on the conjugate detector cell, $D_c(n_c, \text{row}_c)$, i.e., as shown in the following equation:

$$p_{ce}(n,\text{row},\text{view})=P_c(n_c,\text{row}_c,\text{view}_c)-P_{c0}(n_c,\text{row}_c,\text{view}_c) \quad (9)$$

In Step s33, one or more output images are reconstructed using the estimated projection P(n,row,view) on the detector cell D(n,row) with performance difference and the estimated projection error $p_{ce}(n_c, \text{row}_c, \text{view}_c)$ on the conjugate detector cell $D_c(n_c, \text{row}_c)$.

Furthermore, Step s33 comprises: Step s331, subtracting the estimated projection error $p_{ce}(n_c, \text{row}_c, \text{view}_c)$ on the conjugate detector cell $D_c(n_c, \text{row}_c)$ from the estimated projection P(n,row,view) on the detector cell D(n,row) with performance difference to obtain an improved projection $\tilde{P}$(n,row,view), i.e., as shown in the following equation:

$$\tilde{P}(n,\text{row},\text{view})=P(n,\text{row},\text{view})-p_{ce}(n_c,\text{row}_c,\text{view}_c) \quad (10)$$

Step s332, reconstructing one or more output images with the improved projection.

The method for removing streaks from detector cells with performance difference of the third embodiment of the present invention can remove the streaks from the detector cells D(n,row) with performance difference from the reconstructed one or more output images $I_o$ by utilizing a conjugate projection ray of the X-ray source S and utilizing a conjugate projection ray sensed by a conjugate detector cell $D_c(n_c, \text{row}_c)$ to the detector cell D(n,row) with performance difference, estimating an estimation error that is possible to occur on the detector cell D(n,row) with performance difference with a projection error $p_{ce}(n_c, \text{row}_c, \text{view}_c)$ that is possible to occur on the conjugate detector cell $D(n_c, \text{row}_c)$, reducing the estimation error caused by low sampling of the detector cell D(n,row) with performance difference, and reconstructing one or more output images with the improved projection P(n,row,view), thus improving quality of CT reconstructed images.

Although the present invention has been set forth in details in combination with specific embodiments, the person skilled in the art shall be understood that many modifications and variations may be made to the present invention. Therefore, it should be recognized that the intention of the claims is to cover all these modifications and variations within the real concept and range of the present invention.

We claim:

1. A method for removing streaks from detector cells with performance difference, comprising the steps of:
   estimating a projection on a detector cell with performance difference for each of one or more views;
   reconstructing one or more initial images with the estimated projection on the detector cell with performance difference for each view;
   estimating a projection error on the detector cell with performance difference for each view from the reconstructed one or more initial images having streaks; and
   reconstructing one or more output images with the estimated projection error on the detector cell with performance difference for each view to remove the streaks from the reconstructed one or more output images.

2. The method of claim 1, wherein the step of estimating a projection on a detector cell comprises estimating a projection on a detector cell with performance difference using an interpolation method.

3. The method of claim 1, wherein the step of reconstructing one or more output images comprises:
   subtracting the estimated projection error on the detector cell with performance difference from the estimated projection on the detector cell with performance difference to obtain a corrected projection on the detector cell with performance difference; and
   reconstructing one or more output images with the corrected projection on the detector cell with performance difference.

4. The method of claim 3, wherein the step of reconstructing one or more initial images comprises reconstructing one or more initial images with the estimated projection on the detector cell with performance difference using a filter backprojection method, and the step of reconstructing one or more output images comprises reconstructing one or more output images with the estimated projection error on the detector cell with performance difference error using a filter backprojection method.

5. The method of claim 4, wherein the step of estimating a projection error on the detector cell comprises:
   extracting an image stripe along a projection ray of the detector cell with performance difference from the reconstructed one or more initial images; and
   estimating the projection error on the detector cell with performance difference using one or more gray values of one or more pixels in the extracted image stripe.

6. The method of claim 5, wherein the step of estimating a projection error on the detector cell further comprises:
   forming a first straight line between a position of an X-ray source and a position of the detector cell with performance difference;
   selecting second and third straight lines parallel to the first straight line, wherein a distance from the second straight line to the first straight line is the same as a distance from the third straight line to the first straight line; and
   estimating the projection error on the detector cell with performance difference using one or more gray values of one or more corresponding pixels of the first, the second and the third straight lines.

7. The method of claim 6, wherein the step of estimating a projection error on the detector cell further comprises:
   dividing the first straight line into M segments;
   dividing respectively the second and the third straight lines into corresponding M segments as well; and
   computing the projection error on the detector cell with performance difference using the following equation:

$$p_e(n, \text{row}, \text{view}) = e^{-\left(\frac{a}{M}\right)^2} C_1 \sum_{k=1}^{M} \frac{I_s(k,2) - \frac{I_s(k,1) + I_s(k,3)}{2}}{M}$$

wherein $p_e(n,\text{row},\text{view})$ represents the projection error on the detector cell with performance difference, $I_s(k,2)$ represents a gray value of the $k^{th}$ segment on the first straight line, $I_s(k,1)$ represents a gray value of the $k^{th}$ segment on the second straight line, $I_s(k,3)$ represents a gray value of the $k^{th}$ segment on the third straight line, M represents the number of the segments divided, $C_1$ represents a constant mapping a streak level to the projection error on the detector cell with performance difference, and a represents the number of non-zero elements in $I_s(\overline{k},2)$, wherein $$I_s(\overline{k}, 2) = I_s(k, 2) - \frac{I_s(k,1) + I_s(k,3)}{2}, k = [1, M].$$

8. The method of claim 7, wherein the step of estimating a projection error on the detector cell further comprises:
   determining whether the $k^{th}$ segment on individual of the first, the second and the third straight lines is in a pixel range of the reconstructed one or more initial images;
   when it is determined that the $k^{th}$ segment on individual of the first, the second and the third straight lines is not in the pixel range of the reconstructed one or more initial images, the gray value of the $k^{th}$ segment on individual of the first, the second and the third straight lines is zero; and
   when it is determined that the $k^{th}$ segment on individual of the first, the second and the third straight lines is in the pixel range of the reconstructed one or more initial images, the gray value of the $k^{th}$ segment on individual of the first, the second and the third straight lines is interpolated from the reconstructed one or more initial images.

9. The method of claim 6, wherein the distance from the second straight line to the first straight line and the distance from the third straight line to the first straight line are determined by a size of a detector cell of a detector, a distance from the X-ray source to the detector, a distance from the X-ray source to a rotating center of the X-ray source and a reconstruction convolution kernel.

10. A method for removing streaks from detector cells with performance difference, comprising the steps of:
    estimating a projection on a detector cell with performance difference for each of one or more views;
    reconstructing one or more initial images with the estimated projection on the detector cell with performance difference for each view;

computing a possible streak direction for each of one or more pixels in the reconstructed one or more initial images;

identifying a streak feature for each pixel along the possible streak direction;

when identifying a pixel is a streak pixel, smoothing the streak pixel in the streak direction so as to smooth a difference image; and updating one or more output images with the smoothed difference image.

11. The method of claim 10, wherein the step of computing a possible streak direction comprises:

forming a first straight line by an X-ray source and each of one or more pixels in the reconstructed one or more initial images; and defining the possible streak direction for each of one or more pixels in the reconstructed one or more initial images by the first straight line.

12. The method of claim 10, wherein the step of identifying a streak feature comprises:

selecting several pixel points near the pixel along the possible streak direction in the reconstructed one or more initial images;

selecting a second straight line passing each of the several pixel points and perpendicular to the possible streak direction;

for each of the several pixel points, finding two pixel points adjacent to the pixel point in the second straight line;

comparing a gray value of the pixel point to gray values of its adjacent two pixel points; and identifying a streak feature for the pixel using the compared result.

13. The method of claim 12, wherein the step of identifying a streak feature further comprises:

if the gray value of the pixel point is always smaller than the gray values of its adjacent two pixel points for each of the several pixel points, regarding the pixel as a streak pixel; or if the gray value of the pixel point is always bigger than the gray values of its adjacent two pixel points for each of the several pixel points, regarding the pixel as a streak pixel.

14. The method of claim 10, wherein the step of smoothing the streak pixel comprises:

smoothing the streak pixel in the streak direction using the following equation:

$$\tilde{I}(i,j) = w1 \times I1 + w2 \times I(i,j) + w3 \times I2$$

wherein w1, w2 and w3 represent weighting factors, each of the reconstructed one or more initial images is an N×N image, I(i,j) represents a gray value of the streak pixel P(i,j), i,j=[0, N], I1 and I2 respectively represent gray values of the two pixels adjacent to the streak pixel P(i,j) in a second straight line passing the streak pixel P(i,j) and perpendicular to the streak direction, and $\tilde{I}(i,j)$ represents a correct gray value of the streak pixel P(i,j).

15. The method of claim 14, wherein the step of updating one or more output images comprises:

obtaining an output image using the following equation:

$$I_o = I + C_2 \times \text{smooth}(\tilde{I} - I)$$

wherein $I_o$ represents an output image, I represents a reconstructed initial image, $\tilde{I}$ represents a corrected image obtained from $\tilde{I}(i,j)$, smooth represents a smooth operator and $C_2$ represents a parameter for mapping a difference level to $(\tilde{I}-I)$ after the smooth operator.

16. A method for removing streaks from detector cells with performance difference, comprising the steps of:

estimating a projection on a detector cell with performance difference for each of one or more views when an X-ray source is located in each of one or more positions;

estimating a projection error on a conjugate detector cell for a conjugate view when the X-ray source is located in a conjugate position relative to the each position, wherein the each position and its conjugate position are located in a connecting line between the X-ray source and the detector cell with performance difference when the X-ray source is located in the each position; and reconstructing one or more output images using the estimated projection on the detector cell with performance difference and the estimated projection error on the conjugate detector cell.

17. The method of claim 16, wherein the step of estimating a projection on a detector cell comprises:

computing projections on detector cells adjacent to the detector cell with performance difference; and estimating a projection on the detector cell with performance difference with the computed projections on the detector cells adjacent to the detector cell with performance difference using an interpolation method.

18. The method of claim 16, wherein the step of estimating a projection error on a conjugate detector cell comprises:

computing a conjugate projection $P_{c0}$ on the conjugate detector cell for a conjugate view when the X-ray source is located in a conjugate position relative to the each position;

estimating a conjugate projection $P_c$ on the conjugate detector cell for the conjugate view when the X-ray source is located in the conjugate position relative to the each position; and subtracting the computed conjugate projection on the conjugate detector cell from the estimated conjugate projection on the conjugate detector cell to estimate the projection error, $P_c - P_{c0}$ on the conjugate detector cell.

19. The method of claim 18, wherein the step of estimating a conjugate projection $P_c$ further comprises:

computing projections on corresponding conjugate positions of detector cells adjacent to the detector cell with performance difference; and estimating the conjugate projection on the conjugate detector cell with the computed projections on the corresponding conjugate positions of detector cells adjacent to the detector cell with performance difference using an interpolation method.

20. The method of claim 16, wherein the step of reconstructing one or more output images comprises:

subtracting the estimated projection error on the conjugate detector cell from the estimated projection on the detector cell with performance difference to obtain an improved projection on the detector cell with performance difference; and reconstructing one or more output images with the improved projection on the detector cell with performance difference.

* * * * *